United States Patent [19]

Noone

[11] Patent Number: 5,178,540
[45] Date of Patent: Jan. 12, 1993

[54] TOOTH DOWELS

[76] Inventor: Robert Noone, 330 Fitch Ave., Monterey, Calif. 93940

[21] Appl. No.: 857,117

[22] Filed: Mar. 25, 1992

Related U.S. Application Data

[63] Continuation of Ser. No. 625,521, Dec. 11, 1990, abandoned.

[30] Foreign Application Priority Data

Jul. 11, 1990 [GB] United Kingdom ............... 9015233

[51] Int. Cl.$^5$ .............................................. A61C 5/08
[52] U.S. Cl. .................................... 433/220; 433/221
[58] Field of Search ............... 433/210, 211, 220, 221, 433/225

[56] References Cited

U.S. PATENT DOCUMENTS 4,427,383  1/1984  Goldman ............................ 433/220
4,759,714  7/1988  Szegvary ............................ 433/221

FOREIGN PATENT DOCUMENTS 827692   1/1952  Fed. Rep. of Germany ...... 433/220
181016   8/1952  Fed. Rep. of Germany ...... 433/220
848079   9/1952  Fed. Rep. of Germany ...... 433/221
312611   3/1956  Switzerland ........................ 433/221
2162068B 7/1985  United Kingdom .

OTHER PUBLICATIONS

EDS advertisement.
Dentatus advertisement.
Unity advertisement.
Brasseler/Vlock advertisement.
Triax advertisement.
K4/Medidenta advertisement.

Primary Examiner—John G. Weiss
Assistant Examiner—Cindy A. Cherichetti
Attorney, Agent, or Firm—Lowe, Price, LeBlanc & Becker

[57] ABSTRACT

A tooth dowel 10 has a shaft 11 and a coronal restoration frame or head 12 enlarged to provide support for substantially all parts of a total restoration and so constructed as to be relatively readily reducible to fit a restoration of a tooth requiring only a partial restoration. The head includes segmental finger elements 14 adapted to be removed to reduce the size of the head, e.g. by a small disc cutting wheel or pair of snips. A damaged tooth can be rebuilt by (a) obturating (stopping) the root canal, (b) enlarging the coronal portion of the canal, (c) reducing the segments of this tooth dowel appropriately, (d) fixing the so reduced dowel in the canal, and either (e) immediately reducing any remaining coronal tooth structure and fixing a crown on the so reduced tooth and dowel head, or (e1) fabricating a restoration on the dowel head and any remaining tooth structure (FIGS. 2A, 2B), and optionally (e2) reducing the restoration to a core (FIGS. 3A, 3B) and fixing a crown thereon at a later date.

30 Claims, 2 Drawing Sheets

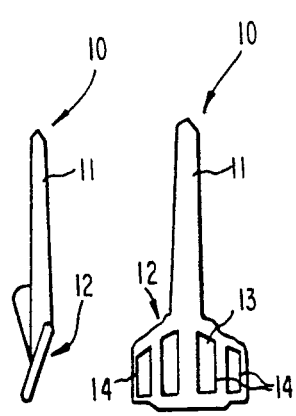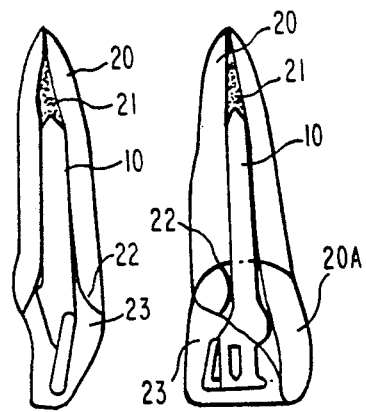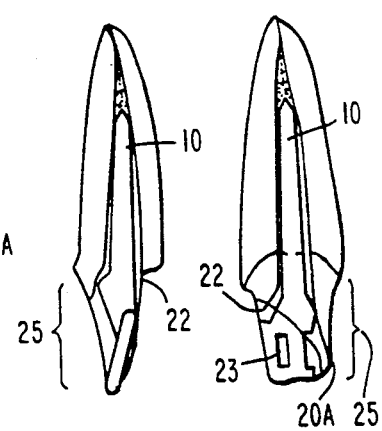
FIG. 1A  FIG. 1B   FIG. 2A  FIG. 2B   FIG. 3A  FIG. 3B
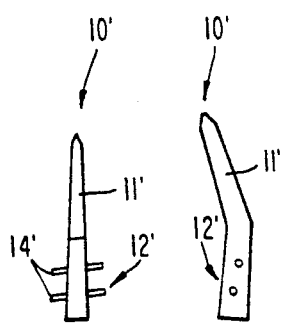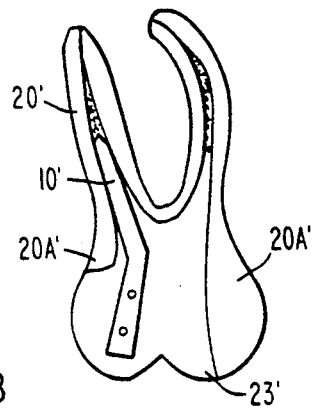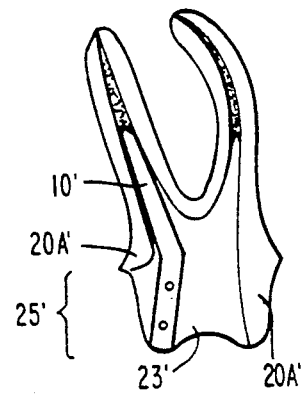
FIG. 4A  FIG. 4B   FIG. 5   FIG. 6
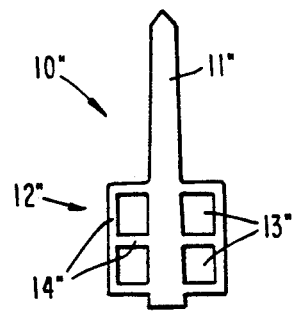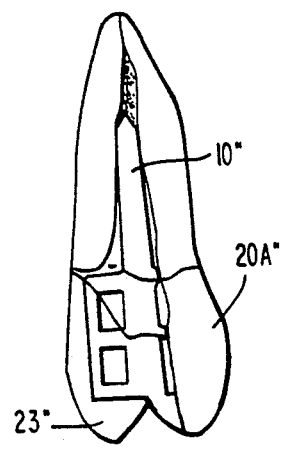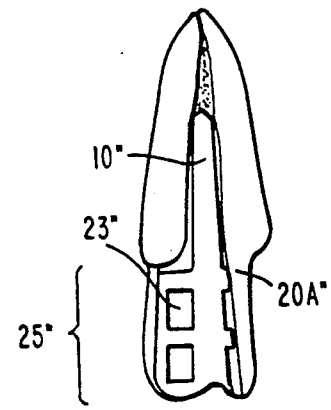
FIG. 7   FIG. 8   FIG. 9

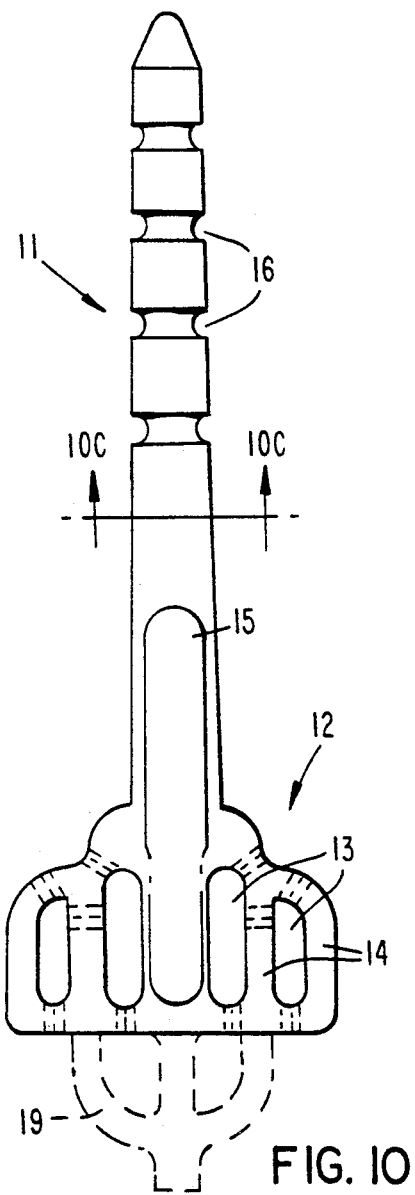
FIG. 10A
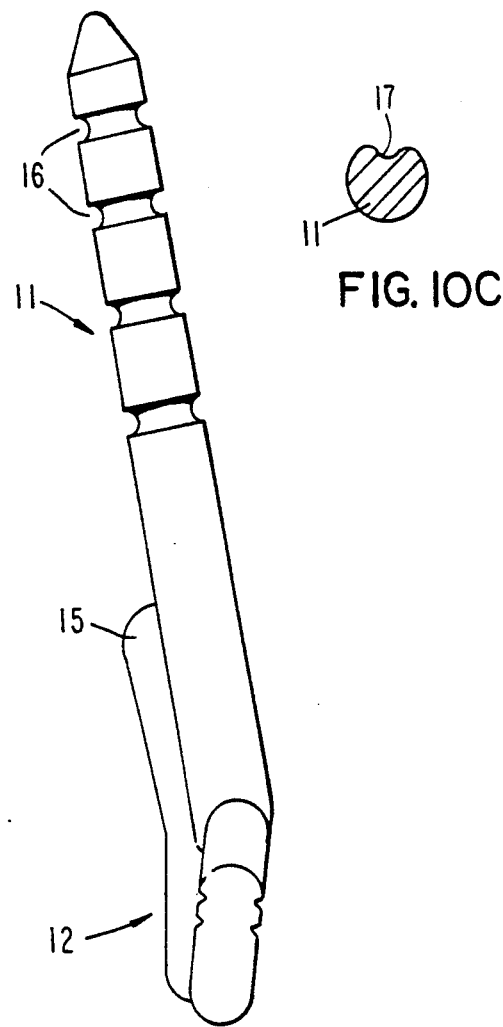
FIG. 10B
FIG. 10C
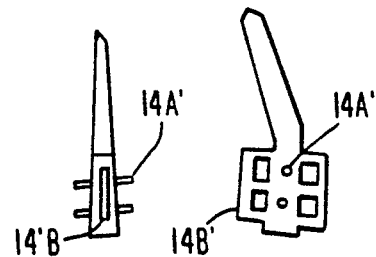
FIG. 11A   FIG. 11B
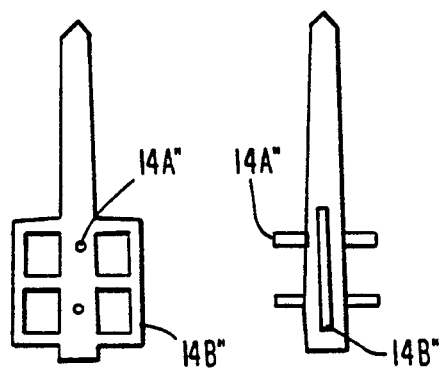
FIG. 12A   FIG. 12B

TOOTH DOWELS

This application is a continuation of application Ser. No. 07/625,521 filed Dec. 11, 1990 now abandoned.

FIELD OF THE INVENTION

The present invention relates to dentistry, and more specifically to root dowels for retaining restorations on tooth roots.

BACKGROUND OF THE INVENTION

There are two major current methods of rebuilding a very damaged tooth, restoration and crowning. Restoration essentially involves building up the damaged tooth by means of a restorative material in situ on the tooth; crowning involves forming a core on the tooth and forming, separately, a crown which is then cemented into place on the core.

Restorations are less time consuming and cheaper than crowning. A crown requires considerably more gross tooth reduction, and may have adverse effects on the periodontum. However, colour matching a restoration to a tooth is somewhat less reliable than colour matching a crown, because restoration is performed extempore, and the colour of a restoration may change gradually with the lapse of time. Restorations are also more liable to wear and to fracture than are crowns.

If a restoration becomes unsatisfactory, it can at some future time be reduced to form a core on which a crown is cemented provided that the original restoration provides adequate support and retention.

The use of dowels has become well established for the retention of core material for crowning. If the tooth is very damaged, the root canal is obturated, the coronal portion of the canal is enlarged, the dowel or post is inserted, core material is adapted to the dowel, and the core material and remaining tooth structure is reduced for crowning.

Various designs of dowel or post for this purpose are available. For example, there are screws of various lengths and diameters; custom castings made to approximate the internal size of the root canal; and parallel stainless steel knurled wired (which may have a vent channel up one side). A specific example of such a dowel is described in my earlier patent no GB 2 162 068 B. All these known dowels are normally fixed in the root canal by means of some form of luting agent (cement), through simple screwing into place has also been proposed.

There are many variations on the precise form of the dowel, which has to have one end firmly fixed in the root canal and in turn have either the restoration or the core firmly attached to its other end. To assist in the latter attachment, various forms of knurling and/or enlargements of the outer end of the dowel have been proposed. A specific is shown in the second embodiment of my earlier patent no GB 2 162 068 B noted above. In this patent is shown a dowel the top end of which has projecting lobes and a jagged top, and adds that the top end of the dowel can be made with a myriad of different shapes to help in retaining the core material to be attached to the dowel.

There is a wide variety of tooth sizes and several tooth types. It was stated in my earlier patent no GB 2 162 068 B noted above that "A set of dowels may be made in a convenient sequence of lengths and tip diameters. It is also possible to make the dowel with an angle or bend near the top end, for use in resetting" (i.e., retaining) "the crown of a projecting (buck) tooth." (Another use of a bent dowel would be to support core material or restoration material when the core or restoration diverges from the long axis of the root canal.) In addition to the various lengths and bends required, the enlargement at the top end of the dowel is also required in a variety of sizes, to allow for the different sizes of restoration or core which may be required. Hence a wide variety of combinations of dowel sizes and shapes may be required.

One object of the present invention is to provide dowel structures which can be used either for a direct crowning or for a restoration which can later be reduced to a core which is then crowned.

SUMMARY OF THE INVENTION

According to one aspect, the invention provides a tooth dowel having a shaft and a coronal restoration frame or head including segmental finger elements adapted to be used in toto, reduced in size, or removed completely, in dependence on the clinical situation at hand. The fingers may be attached to each other at their outer ends, preferably forming a plate-like structure having holes enclosed by the fingers. The holes may be arranged generally as a sequence transverse to the shaft, or as a sequence one beyond the other in the direction of the shaft, or as an array or combination of such sequences having a plurality of sequences one beyond the other with the holes in each sequence transverse to the shaft. In the latter two cases, the overall length of the dowel is preferably reducible by removing all parts of the head, including any central or spine portion, forming a transverse sequence of holes.

The fingers may alternatively be attached to the remainder of the dowel only at their inner ends. The fingers are in this case preferably substantially cylindrical with lengths greater than their diameters, to facilitate their cutting as clinical situations present.

The shaft may be provided with grooves around it, and the fingers may likewise be formed with slight grooves around them, to assist in retention of the dowel in the root canal and the core or restoration on the dowel. The grooves may also assist the user in measurement of the required degree of reduction.

The dowel may have a rib-like projection or thickening along the upper part of the shaft and the head to strengthen it and assist in preventing rotation.

Since the dowel is required to have adequate strength to retain a tooth core and crown, it is envisaged that any trimming of the dowel would normally be done by a suitable tool, such as a small disc cutting wheel or pair of snips.

It will be realized that these features also allow the rquired variety of dowels to be reduced.

According to another aspect, the invention provides a method of rebuilding a damaged tooth comprising the steps of (a) obturating (stopping) the root canal, (b) enlarging the coronal portion of the canal, (c) reducing the segments of a tooth dowel having a shaft and a coronal restoration frame or head as appropriate to a size on which a restoration of the remaining parts of the tooth can be fabricated, the head including segmental finger elements adapted to be so reduced, (d) fixing the so reduced dowel in the canal, and either (e) immediately reducing any remaining coronal tooth structure and fixing a crown on the so reduced tooth and dowel head, or (e1) fabricating a restoration on the dowel head and any remaining tooth structure and optionally (e2) reducing the restoration to a core and fixing a crown thereon at a later date.

Preferably the dowel used in the method also has a suitable combination of the further features set out above.

As noted above, the head of the dowel must have the restoration or core firmly attached to it. It is further desirable for the dowel head to provide support and strength for the restoration or core attached to it. However, the shape and volume of a tooth to be replaced, particularly in a restoration, is highly variable. It is not practicable to provide dowels which are in effect "tailor-made" for such situations. Thus although there is a very wide variety of dowel head shapes available, they all conform to a small number of fairly standard types. The head can be relatively small and compact; it can be lengthened to a certain degree, and be thickened to a certain degree (relative to the dowel shaft), usually by means of lobes or other projection-like features which promote interlocking with the core or restoration material. It is also known for the dowel head to be expanded towards its junction with the dowel shaft.

We have realized that it is possible to so design the dowel head that it spreads out to give a wide support at its outer end and can be readily reduced to conform with the shape and volume of tooth to be replaced, particularly in a restoration.

According to a further aspect of the invention, therefore, there is provided a tooth dowel having a shaft and a coronal restoration frame or head enlarged to provide support for substantially all parts of a total restoration and so constructed as to be relatively readily reducible to fit a restoration of a tooth requiring only a partial restoration. The head is thus preferably of a length approaching that of a normal tooth crown and its outer end of a width approaching that of a normal tooth crown. The head is preferably a generally flat character and provided with apertures therein or deep indentations from its boundary, to facilitate the reduction of the head to fit whatever clinical situation of partial retaining of tooth material may present itself.

DETAILED DESCRIPTION OF EMBODIMENTS OF THE INVENTION

Various preferred forms of dowel in accordance with the invention will now be described, by way of example, with reference to the drawings, in which:

FIGS. 1A and 1B are views of a first form of dowel;

FIGS. 2A and 2B are corresponding views of a tooth including the FIG. 1 dowel after restoration;

FIGS. 3A and 3B are corresponding views of the same tooth after reduction of the restoration to a core for crowning;

FIGS. 4A and 4B are views of a second form of dowel;

FIG. 5 is a corresponding view of a tooth including the FIG. 4 dowel with a restoration;

FIG. 6 is a view corresponding to FIG. 4B of the same tooth after reduction of the restoration to a core for crowning;

FIG. 7 is a view of a third form of dowel;

FIG. 8 is a corresponding view of a tooth including the FIG. 7 dowel with a restoration;

FIG. 9 is a corresponding view of the same tooth after reduction of the restoration to a core for crowning;

FIGS. 10A to 10C are enlarged and more detailed views of the FIGS. 1A and 1B dowel;

FIGS. 11A and 11B are views of a modification of the dowel of FIGS. 4A and 4B; and FIGS. 12A and 12B show a modification of the dowel of FIG. 7.

FIGS. 1A and 1B are front and side views of a form of dowel 10 suitable for use with an incisor tooth. As seen, the dowel consists of a rod-like portion or shaft 11 and a head 12. The head 12 is plate-like, and is at a slight angle to the rod portion 11, as seen FIG. 1B. The head 12 has four holes 13 formed in it, so that it consists of several fingers 14.

In FIGS. 2A and 2B are shown an incisor tooth root 20 which has an oblique fracture from incisal to proximal. The root canal has been obturated by a stopping agent 21 at the bottom end, and has been drilled above the obturation to create space for the dowel. The dowel 10 has been inserted into the drilled root canal, and fixed by means of a luting agent 22, which is preferably an agent which forms a strong bond with dentine (since the interior of the tooth is dentine), and a restoration 23 has been formed on the coronal end of the tooth.

It will be noted particularly that the tooth root 20 has a projecting portion 20A at its coronal end which is sound and has therefore been left in position, rather than being ground away. This projecting portion 20A restricts the permissible size of the head of the dowel. The head of the dowel 10 is too large, and the projection 20A would interfere with it. However, the dowel 10 can nevertheless be used with the root 20, and this problem be overcome, by cutting off those fingers of the head which would interfere with the projection 20A.

The cement or luting agent used to fix the dowel 10 in the drilled tooth canal desirably has suitable properties for chemical setting, bonding to dentine, bonding to the dowel, and inhibition of caries. The material used for the restoration 23 desirably has suitable properties for command setting (e.g. light activated setting) and bonding to the cement, dentine, and the dowel, colour matching to the tooth, and resistance to wear. The cement and the restoration material will therefore in general be different. However, the cement alone can be used, particularly if there is no intermediate restoration phase (i.e. a core is formed directly to receive a crown).

The core which results when the restoration is reduced for crowning will invariably include the dowel (possibly reduced), and will also include the luting cement, the restorative material (if that is different from the luting cement), and/or some remaining parts of the tooth.

FIGS. 3A and 3B show the same tooth with the restoration reduced to a core 25 in readiness for a crown (not shown) to be cemented to it. This reduction could possibly be performed some years after the original restoration.

FIGS. 4A and 4B are corresponding views of a form of dowel 10' suitable for use with a molar. FIG. 5 shows a molar tooth root 20' with a projection 20A' on its coronal portion and with the dowel 10' fixed in it and a restoration 23'. FIG. 6 shows the same tooth root with the restoration 23' reduced to a core 25' in readiness for crowning.

The dowel 10' has projecting peg-like fingers 14' formed on its head 12'. With the tooth 20' shown, the head of the dowel is not restricted by the tooth, and the dowel can be used for a restoration in toto, though if the remaining tooth structure were more extensive, the dowel could still be used, by cutting off those parts of the head which would interfere with the remaining parts of the tooth. The bend in the dowel is desirable because the inclination of the root would place a straight dowel in the centre of the crown, resulting in the left-hand portion of the core material (as seen in FIG. 5) being unsupported.

FIG. 7 is a corresponding view of a form of dowel 10'' suitable for use with a straight tooth such as a premolar. FIG. 8 shows such a tooth root 20'' with a projection 20A'' on its coronal portion and with the dowel 10'' fixed in it and a restoration 23''. FIG. 9 shows the same tooth root with the restoration 23'' reduced to a core 25'' to which a crown (not shown) is about to be attached.

The head 12'' of the dowel 10'' is plate-like, and is in line with the rod portion 11''. The head 12'' has four holes 13'' formed in it, so that it consists of several fingers 14''. As with the tooth of FIGS. 2 and 3, the projecting portion 20A'' restricts the permissible size of the head of the dowel 10'', which is too large. However, the dowel 10'' can nevertheless be used with the root 20'', and this problem be overcome, by cutting off those fingers of the head which would interfere with the projection 20A''.

It will be noted that if the two top fingers of the dowel 10'' of FIG. 7 are cut off, the central upper portion of the head can also be cut off, so reducing the overall length of this dowel.

FIGS. 10A and 10B are enlarged and more detailed views of the dowel of FIGS. 1A and 1B. It will be seen that the shaft 11 is substantially cylindrical, with a diameter somewhat greater than the thickness of the head 12. A rib-like projection 15 along the upper part of the shaft 11 and the head 12 strengthens the dowel and assists in preventing rotation. Also, the shaft 11 has grooves 16 formed at intervals along it to assist in retention of the dowel. (The grooves may also assist in measurement for reduction.) The head portion may optionally be provided with similar grooves, to facilitate trimming to shape (e.g. by grinding or by the use of small snips) and/or measurement for such reduction.

The shaft of the dowel is preferably also provided with a longitudinal groove 17, as shown in FIG. 10C, which is a section through the shaft 11 of the dowel of FIGS. 1A and 1B. This groove provides a path through which the cement 21 may pass if the dowel is inserted into a tight-fitting channel in the tooth 20, allowing relief of the pressure which might otherwise be built up in the root of the tooth. The groove 17 may conveniently be located on the opposite side of the shaft from the projection 15.

The other dowels shown may be similarly grooved with grooves around their shafts, across their head portions, and/or their shafts.

The dowels may conveniently be formed by casting, with the metal entering the mould at the head end of the dowel through a constriction at which the dowel can conveniently be broken off from the feed rod of casting metal. In the case of dowels having particularly broad heads, such as the dowel shown in FIG. 10B, a plurality of feed paths to the mould may be desirable, as indicated at 19.

Identification data may be formed on the dowels to indicate their shaft diameters. This data may be located at any suitable place on the dowels; a convenient place is in the region where the head and shaft meet.

The heads of the dowels described so far had a broadly planar structure, with the fingers have projected outwards on the opposite sides from the centre line of the head. It may be advantageous for the head structure to be non-planar, with fingers projecting outwards from the centre line of the head in several directions.

FIGS. 11A and 11B are views, in two perpendicular directions, of such a modification of the dowel of FIGS. 4A and 4B, in which there are two sets of fingers. Fingers 14A' project out in one plane, while fingers 14B' project out in a perpendicular plane. In FIGS. 12A and 12B are shown a similar modification of the dowel of FIG. 7, with finger structures 14A'' and 14B'' projecting out in perpendicular planes. The dowel of FIGS. 1A and 1B could obviously be modified similarly if desired.

It will be noted that the finger structures 14A' and 14A'' are peg-like, while the finger structures 14B' and 14'' have a looped or plate-like structure. This is because if both structures were looped, the casting would be more difficult.

It is a general characteristic of all the dowels described with reference to the drawings that the overall diameter of the head structure, taken in a plane perpendicular to the axis of the dowel, is substantially the same or increasing over a substantial part of the head structure as the plane is moved away from the shaft. Also, in those dowels in which the heads have peg-like fingers, the length of the fingers is greater than their diameter.

I claim:

1. A tooth dowel having a design suitable for use for partial or maximum restoration of different types of teeth comprising a rod-like portion extending from a head having an enlarged segment extending transversely from a longitudinal axis of the rod-like portion, the enlarged segment being symmetrical with respect to the longitudinal axis, the rod-like portion having a size and shape adapted to fit into a root canal of a tooth, the head enlarged segment having a size and shape adapted to fit into a coronal end of the tooth, the head including a structure enabling the enlarged region to be reduced in size along a predetermined region extending parallel to the longitudinal axis so that, with a total or near total restoration, the head size is not usually altered, and with a partial restoration, the enlarged head segment is reduced in size along the region prior to insertion of the tooth dowel with the tooth.

2. The tooth dowel of claim 1 wherein the dowel has a rib-like projection along an upper part of the shaft and the head to strengthen the dowel and assist in preventing rotation thereof.

3. The tooth dowel of claim 1 wherein the head structure is constructed and arranged to enable the enlarged region to be reduced in size along plural regions generally extending parallel to the axis.

4. The tooth dowel of claim 3 wherein the structure includes plural fingers each having a longitudinal axis extending parallel to the longitudinal axis of the rod-like portion.

5. The tooth dowel of claim 4 wherein the fingers lie in a plurality of planes about the long axis of the rod-like portion.

6. The tooth dowel of claim 4 wherein each finger is spaced from an adjacent element that extends in the direction of the longitudinal axis by a gap.

7. A tooth dowel according to claim 6 wherein the fingers are attached to the remainder of the dowel only at their inner ends.

8. The tooth dowel of claim 6 wherein the fingers are substantially cylindrical with lengths greater then their diameters.

9. A tooth dowel according to claim 6 wherein the fingers are formed with slight grooves around them.

10. The tooth dowel of claim 6 wherein the gap extends longitudinally substantially along the entire length of the finger.

11. The tooth dowel of claim 10 wherein the adjacent element is another finger.

12. The tooth dowel of claim 10 wherein the adjacent element is the rod-like portion.

13. The tooth dowel of claim 6 wherein opposite ends of each finger are connected to said element adjacent thereto.

14. The tooth dowel of claim 13 wherein intermediate portions of each finger are connected to said element adjacent thereto.

15. The tooth dowel of claim 6 wherein intermediate portions of each finger are connected to said element adjacent thereto.

16. The tooth dowel of claim 1 further including a support structure extending substantially at right angles to the head and the rod-like portion adapted to fit into the coronal end of the tooth.

17. The tooth dowel of claim 16 wherein the support structure comprises a rib-like porjection that extends longitudinally in the direction of the rod-like portion longitudinal axis.

18. The tooth dowel of claim 16 wherein the support structure includes peg-like members each having a longitudinal axis extending radially from the longitudinal axis of the rod-like portion.

19. The tooth dowel of claim 1 wherein the rod-like portion includes a first groove that extends in the direction of the longitudinal axis to provide a path for cement to flow along.

20. The tooth dowel off claim 19 wherein the rod-like portion includes a second groove approximately at right angles to the first groove.

21. The tooth dowel of claim 1 wherein said rod-like portion is approximately in line with the head enlarged segment.

22. The tooth dowel of claim 21 wherein said enlarged head includes a pair of tapered side edges extending outwardly in opposite directions from a region of the rod-like portion remote from both longitudinal ends of the dowel and toward the end of the dowel adapted to be inserted in the coronal end of the tooth.

23. The tooth dowel of claim 21 wherein said enlarged head includes a pair of substantially parallel edges extending generally parallel to the longitudinal axis of the rod-like portion.

24. A tooth dowel having a design suitable for use for partial or maximum restoration of different types of teeth comprising a rod-like portion extending from a head having an enlarged segment extending transversely from a longitudinal axis of the rod-like portion, the rod-like portion having a size and shape adapted to fit into a root canal of a tooth, the head enlarged segment having a size and shape adapted to fit into a coronal end of the tooth, the head including a structure enabling the enlarged region to be reduced in size along a predetermined region extending parallel to the longitudinal axis so that, with a total or near total restoration, the head size is not usually altered, and with a partial restoration, the enlarged head segment is reduced in size along the region prior to insertion of the tooth dowel with the tooth said enlarged head including a pair of tapered side edges extending outwardly in opposite directions from a region of the rod-like portion remote from both longitudinal ends of the dowel toward the end of the dowel adapted to be inserted in the coronal end of the tooth.

25. A method of partially restoring a damaged tooth with a tooth dowel having a head with an enlarged region extending transversely from a longitudinal axis of a rod-like portion of the dowel, comprising the steps of:
   (a) obturating the tooth root canal,
   (b) enlarging the tooth canal coronal portion,
   (c) reducing the size of the head as appropriate to a size on which a restoration of the remaining parts of the tooth can be fabricated,
   (d) fixing the so reduced dowel in the canal,
   (e) immediately thereafter reducing any remaining coronal tooth structure, and
   (f) fixing a crown on the so reduced tooth and dowel head.

26. A method of partially restoring a damaged tooth with a tooth dowel having a head with an enlarged region extending transversely from a longitudinal axis of a rod-like portion of the dowel, comprising the steps of:
   (a) obturating the tooth root canal,
   (b) enlarging the tooth canal coronal portion,
   (c) reducing the size of the head as appropriate to a size on which a restoration of the remaining parts of the tooth can be fabricated,
   (d) fixing the so reduced dowel in the canal, and
   (e) fabricating a restoration on the dowel head and any remaining tooth structure.

27. The method of claim 26 further comprising reducing the restoration resulting from step (e) to a core and fixing a crown thereon at a later date.

28. A method of using first and second tooth dowels having the same size and shape for maximum and partial restoration of first and second different teeth, respectively, each tooth dowel including a rod-like portion extending from a head having an enlarged segment extending transversely from a longitudinal axis of the rod-like portion, the rod-like portion having a size and shape adapted to fit into a root canal of a tooth, the head enlarged segment having a size and shape adapted to fit into a coronal end of the tooth, the head including a structure enabling the enlarged region to be reduced in size, the method comprising
   (a) obturating the root canal of the first tooth,
   (b) enlarging the canal coronal portion of the first tooth,
   (c) reducing the size of the head of the first dowel as appropriate to a size on which a restoration of the remaining parts of the first tooth can be fabricated,
   (d) fixing the so reduced first dowel in the canal of the first tooth,
   (e) obturating the root canal of the second tooth,
   (f) enlarging the coronal portion of the second tooth canal, and
   (g) fixing the second dowel in substantially unaltered form in the obturated second root canal with the enlarged coronal portion.

29. The method of claim 28 further including reducing the head of one of the dowels after it has been fixed in the root canal of the respective tooth and while it is in situ in the root canal of the respective tooth, and fabricating a restoration on the dowel head and any remaining structure of the respective tooth.

30. The method of claim 29 further including reducing the restoration fabricated by the step defined in the previous claim and fixing a crown thereon.

* * * * *